United States Patent
Tamminga et al.

(10) Patent No.: US 11,970,726 B2
(45) Date of Patent: Apr. 30, 2024

(54) METHOD FOR QUANTIFYING THE CULTIVABILITY OF INDIVIDUAL BACTERIAL CELLS USING CULTURE INDEPENDENT PARAMETERS

(71) Applicant: Dutch Water Technologies B.V., Sneek (NL)

(72) Inventors: Gerrit Geert Tamminga, Leeuwarden (NL); Antonius Johannes Hendrikus Hyacinthus Engelaar, Oppenhuizen (NL); Gijsbert Johan Jansen, Sneek (NL)

(73) Assignee: Dutch Water Technologies B.V., Sneek (NL)

( * ) Notice: Subject to any disclaimer, the term of this patent is extended or adjusted under 35 U.S.C. 154(b) by 1158 days.

(21) Appl. No.: 16/627,702

(22) PCT Filed: Jun. 28, 2018

(86) PCT No.: PCT/NL2018/050419
§ 371 (c)(1),
(2) Date: Dec. 30, 2019

(87) PCT Pub. No.: WO2019/004830
PCT Pub. Date: Jan. 3, 2019

(65) Prior Publication Data
US 2020/0165654 A1 May 28, 2020

(30) Foreign Application Priority Data

Jun. 28, 2017 (EP) .................................... 17178309

(51) Int. Cl.
*C12Q 1/02* (2006.01)
*G01N 21/64* (2006.01)
*G06F 17/18* (2006.01)

(52) U.S. Cl.
CPC ........... *C12Q 1/02* (2013.01); *G01N 21/6458* (2013.01); *G06F 17/18* (2013.01)

(58) Field of Classification Search
CPC .............................. G01N 21/6458; C12Q 1/02
See application file for complete search history.

(56) References Cited

FOREIGN PATENT DOCUMENTS

| AU | 2014217946 A1 * | 8/2015 | ......... G01N 21/0303 |
|----|-----------------|--------|------------------------|
| WO | WO9531481       | 11/1995 |                       |
| WO | WO-9531481 A1 * | 11/1995 | ............. C07K 16/12 |
| WO | WO9717463       | 5/1997 |                        |
| WO | WO-9717463 A1 * | 5/1997 | ................ C12Q 1/04 |

OTHER PUBLICATIONS

The Britannica Dictionary "reflective" 1 pg, https://www.britannica.com/dictionary/reflective, accessed Jul. 1, 2023 (Year: 2023).*
Longman Dictionary of Contemporary English Online "reflective" 1 pg. https://www.ldoceonline.com/dictionary/reflective, accessed Jul. 1, 2023 (Year: 2023).*
Oxford Learners Dictionaries "Reflective" 1 pg, https://www.oxfordlearnersdictionaries.com/us/definition/english/reflective, accessed Jul. 1, 2023 (Year: 2023).*
International Search Report and Written Opinion issued in PCT/NL2018/050419 dated Aug. 28, 2018, 10 pages.
Villarino, Andrea et al., "Exploring the frontier between life and death in *Escherichia coli*: Evaluation of different viability markers in live and heat- or UV-killed cells," Research in Microbiology, vol. 151, pp. 755-768, 2000, 14 pages.
Besnard, V., et al., "Development of a direct viable count procedure for the investigation of VBNC state in Listeria monocytogenes," Letters in Applied Microbiology, vol. 31, pp. 77-81, 2000, 5 pages.
Hammes, Frederik, et al., "Cultivation-independent Assessment of Bacterial Viability," Advances in Biochemical Engineering/Biotechnology, vol. 124, pp. 123-150, 2011, 28 pages.
Garcia-Hernandez, J., et al., "A combination of direct viable count and fluorescence in situ hybridization for specific enumeration of viable *Lactobacillus delbrueckii* subsp. *bulgaricus* and *Streptococcus thermophilus*," Letters in Applied Microbiology, vol. 54, 2011, pp. 247-254, 8 pages.
Garcia Armisen, T., et al., "Combining direct viable count (DVC) and fluorescent in situ hybridisation (FISH) to enumerate viable *E. coli* in rivers and wastewaters," Water Science and Technology, vol. 50, No. 1, pp. 271-275, 5 pages.

* cited by examiner

*Primary Examiner* — Thane Underdahl (74) *Attorney, Agent, or Firm* — Faegre Drinker Biddle & Reath LLP (57) ABSTRACT

The invention relates to the field of microbiology and detecting micro-organism. Provided is a method for the quantitative analysis of microbial cells in a liquid sample, comprising the steps of (i) contacting the sample with a nucleic acid binding fluorescent dye to stain for nucleic acids in said microbial cells; (ii) subjecting the labelled cells to a fluorescence microscopy imaging method and determining, based on the nucleic acid staining, for a plurality of single cells at least a first parameter reflecting the nucleic acid content of said cell and a second parameter reflecting the extent of stretching of said cell; (iii) classifying based on said at least first and second parameter said cell into one of the following categories: (A) Viable cultivable cells with a nucleic acid content value between $>=0.1$ and $<1.0$ and extent of stretching of the cell value between $>=1.0$ and $10$ $\mu\eta m^2$, (B) Viable non-cultivable cells with a nucleic acid content value of $>-0.2$ and extent of stretching of the cell value of $>=0.5$ $\mu\eta m^2$ minus (A), (C) Most likely dead cells with a nucleic acid content of $<1.0$ and extent of stretching of the cell value of $<0.50$ $\mu\eta m^2$; and (iv) calculating the ratio of the amount of (A) viable cultivable cells, (B) viable non-cultivable cells and (C) most likely dead cells in a microbial sample.

13 Claims, 6 Drawing Sheets

METHOD FOR QUANTIFYING THE CULTIVABILITY OF INDIVIDUAL BACTERIAL CELLS USING CULTURE INDEPENDENT PARAMETERS

The invention relates to the field of microbiology and detecting micro-organisms. More in particular, it relates to a method for the quantitative analysis of the metabolic state of individual microbial cells in a liquid sample.

Nowadays, standard microbiology laboratories need low-cost, fast, reliable and viable bacterial cell counting methods. Bacterial contamination, in any form and any matrix is monitored for various reasons. Frequently, microbiology laboratories make use of classical bacterial analyses of quantification by the classic microbiological culturing method ("the golden standard"). This method is currently over 100 years old and is able to detect the cultivable fraction of micro-organisms only. This method is time proven and has a low cost. However, major drawbacks of this method include the Time-To-Result (minimum 2 days) and the fact that both dead cells and viable non-cultivable cells are not detected.

Counting bacterial cells sounds trivial, but not all bacterial cells are able to form visible colonies on solid medium plates. Even within pure cultures, it is known that the rate of colony formation is not uniform and that several cells might form only micro colonies ("self-limiting" growth behaviour), and therefore bacterial cell counts cannot be detected conveniently by the naked eye (Breeuwer and Abee, 2000; Zengler, 2009).

Those bacterial cells, which are not growing on standard solid medium plates, are often designated as viable but non cultivable (VBNC) (Oliver, 2005). Variation of the components (e.g. 22 components, 2 different concentrations) used to create a solid medium in order to provide a suitable growth basis for all cells would require about $10^{15}$ medium compositions; which is simply not feasible (Williams et al., 1998; Zengler, 2009).

Therefore different staining techniques were invented to differentiate living bacterial cells from dead bacterial cells. One example is the LIVE/DEAD BacLight staining kit (Invitrogen) (Boulos et al., 1999). The kit consists of two stains, Propidium Iodide (PI) and SYTO9, which are both intercalating agents, allowing a differentiation between bacteria with damaged cytoplasmic membranes and intact membranes. PI is only able to enter bacterial cells with damaged cytoplasmic membranes (red stained bacteria) and SYTO9 is entering all bacterial cells (green stained bacteria).

Red stained bacterial cells are most likely no longer cultivable (non-viable/dead) whereas green cells are most likely cultivable bacterial cells (viable). In practice an intermediate physiological state may exist. This leads to difficulties in the interpretation of the data (e.g. effectiveness of disinfection or antibiotics) (Berney et al., 2007).

Well known parameters of bacterial viability are cell wall integrity, cell elongation, formation of ribosomal RNA, fluorescence intensity of DNA-specific staining, enzymatic activity and intact polar membrane lipids (Breeuwer and Abee, 2000; Flemming, 2013; Hammes et al., 2011). The LIVE/DEAD BacLight staining kit is based upon on the cell wall integrity solely.

In summary, current microbial enumeration testing is dominated by microbial culture. Microbial culture has the important advantages of being simple, ultra-sensitive, inexpensive, and quantitative but has the significant drawback of being slow (e.g. incubation time over 24 hours). The long time required for results has major costs in healthcare (e.g. unnecessary treatment of antibiotics) and in manufacturing (e.g. call-back of beverage or food). More rapid methods which can give the results within 4 or 8 hours have been developed (e.g. polymerase chain reaction (PCR), antigen-antibody and other biomarkers), but while improving the time to results, they have sacrificed two of the most critical advantages of microbial culturing. The first sacrifice was the possibility to select the cultivable bacterial cells and the second sacrifice is the sensitivity.

Recognizing the need for a test that is faster than traditional microbial culture but that retains the key benefits of the traditional method, the present inventors therefore set out to develop a truly rapid method (e.g. time-to-result less than 4 hours) to detect micro-organisms which method also provides reliable information, in particular about the metabolic status of the bacterial cells in the sample.

These goals were met by the provision of a method relying on a new principle comprising a unique combination of different steps. The method is characterized among others by the use of two culture-independent parameters (nucleic acid content per cell and extent of stretching of the cell) as a means of estimating the number of viable cultivable cells, viable non-cultivable cells and most likely dead cells in a microbial population.

In one embodiment, the invention provides a method for the quantitative analysis of (viable) microbial cells in a liquid sample, comprising the steps of
  (i) contacting the sample with a nucleic acid binding fluorescent dye to stain cellular nucleic acids in said microbial cells;
  (ii) subjecting the labelled cells to a fluorescence microscopy imaging method and determining, based on the nucleic acid staining, for a plurality of single cells at least a first parameter reflecting the nucleic acid content of said cell and a second parameter reflecting the extent of stretching of said cell;
  (iii) classifying based on said at least first and second parameter said cell into one of the following categories:
    (A) Viable cultivable cells with a nucleic acid content value between ≥1 and <1.0 and extent of stretching of the cell value between ≥1.0 and 10 $\mu m^2$,
    (B) Viable non-cultivable cells with a nucleic acid content value of >−0.2 and extent of stretching of the cell value of ≥0.5 $\mu m^2$, minus the Viable cultivable cells under (A), and
    (C) Most likely dead cells with a nucleic acid content of <1.0 and extent of stretching of the cell value of <0.5 $\mu m^2$.
  (iv) calculating the ratio of the amount of (A) viable cultivable cells, (B) viable non-cultivable cells and (C) most likely dead cells in a microbial sample.

Herewith, the invention provides a method for (autonomous) quantification of the cultivability of individual bacterial cells using culture independent parameters. A method provided herein is applicable to any sample which may contain microbial cells. For example, the sample is selected from the group consisting of water samples, clinical samples, beverages, dairy products, and liquid growth media. In a preferred embodiment, the sample is selected from the group consisting of: respiratory, urogenital, reproductive tract, central nervous system, urine, blood, dermal, plasma, serum, saliva, wound tissue, wound exudate, biopsy, faeces, reproductive tract, and solid tissue samples, and derivatives thereof. The sample is typically isolated from a mammalian subject, preferably a human subject. However, veterinary application of the method provided herein is also encompassed. In fact, as will be appreciated by a person skilled in the art, the principle as disclosed in the present invention is applicable for measuring the vitality of all known microbial species in the following matrices: all types of process water, drinking water, surface water, groundwater, ballast water, veterinary and medical liquids, liquid microbiological media, all beverages, and all dairy products.

The microbial cells may comprise bacterial cells, yeast cells, fungal cells, parasitic cells or any combination thereof.

In step (i) of the method, the sample is contacted with a nucleic acid binding fluorescent dye to stain cellular nucleic acids (DNA, RNA, mRNA) and determine the nucleic acid content of said microbial cells. This step comprises fixation and dehydration of microbial cells. Fluorescent dyes and associated protocols to stain cellular nucleic acid are known in the art. For example, it comprises staining cells with an intercalating agent such as propidium iodide (PI), SYBR Green I, YO-PRO-1, TOTO-3, or TO-PRO-3, preferably PI.

In a specific aspect, a method of the invention comprises a protocol which differs slightly from the normal application of using an intercalating agent, like propidium iodide, namely fixation of microbial cells using formaldehyde or paraformaldehyde; dehydration of cells using 96% alcohol; addition of an intercalating agent (e.g. dissolved in milliQ) and washing off free intercalating agent to increase the signal-to-noise-ratio.

Step (ii) comprises subjecting the labelled cells to a fluorescence microscopy imaging method and determining, based on the nucleic acid staining, for a plurality of single cells at least a first parameter reflecting the nucleic acid contents of said cell and a second parameter reflecting the extent of stretching of said cell. In a specific embodiment, step (ii) comprises subjecting the cells to a filter cytometry process (e.g. Solid Phase Cytometry (SPC)) to stain, scan, detect, and count fluorescently labelled microbial cells on the surface area of a membrane filter. A preferred optical system uses lenses, camera and an (ultra-violet) light source to visualize microbial cells, such as a fluorescence microscope, or an autonomous operating bioanalysis platform like the AquaScope® (BioTrack BV, Sneek, The Netherlands). The AquaScope® can be applied in the rapid bio monitoring of specific micro-organisms both in the laboratory as well at a remote test site of choice. It combines the reliability and time tested principle of filter cytometry with the speed of analysis. The AquaScope® is capable of measuring numbers of (a) specific micro-organisms in liquid samples ranging from 1 ml to 500 ml. with an additional pre-concentration step, when appropriate. Sample volumes of 2 liters are achievable. It can operate autonomously while inline, in-process or in lab.

It is preferred that, prior to subjecting the labelled cells to a fluorescence microscopy imaging method, the optical part of a fluorescence microscopic unit is calibrated. The calibration must be done by the following two procedures.

The first calibration procedure is the optical lining of the fluorescent optical unit using a micro scale measuring staff, the surface area of a microbial cell can be quantified ($\mu m^2$). This parameter may be used as an indicator for the extent of stretching of the cell.

In a specific embodiment, determining said at least first and second parameter comprises analysis of a crude fluorescence microscopic image using a thresholding algorithm to obtain a binary filter image, and making an overlay of the binary and crude filter image to determine the average grey value, standard deviation and surface area of individual microbial cells.

Typically, it comprises acquiring images under ultra-violet illumination, using a fluorescence microscopic unit mounted with a Charge Coupled Device (i.e. a "digital" camera). The resulting photos are then analysed, using software which automatically filters noise, binarizes the grey-scale image and quantifies light-intensity per object. Selective data acquisition ensures that the data meet certain criteria. In particular, ensuring that the average grey value should not exceed 254 and shall not be less than the average background of the raw image. In addition, an estimate of the surface of the actual image is made, since this value depends on the optical magnification. For example, at the magnification of the Aqua scope (200×) all objects consisting of ≈0.7±0.2 $\mu m^2$ are regarded as "noise".

In a preferred embodiment, a method of the invention uses a thresholding algorithm according to WO2010/040371, herein incorporated by reference, which discloses how a binary image can be created and interpreted. In addition to these algorithms, it must be mentioned that, based on the binary image, an overlay is preferably projected onto the greyscale image. This overlay is used to measure i) the average grey value, standard deviation of the intensity and iii) the area per selected microbial cell.

Preferably, once the average grey value, the standard deviation and surface area per microbial cell is measured, the nucleic acid content can be calculated on the basis of the following equation 1;

$$\text{nucleic acid content} = \frac{\log(\text{standard deviation per microbial cell})}{\log(\text{average grey value per microbial cell})}$$

The second calibration procedure is to establish the optimal exposure time by means of a so called "light titration". Six different cultures were stained, imaged (a light titration consisting of the acquisition of digital images at exposure times varied from 10-100 ms with steps of 10 ms, from 100-1000 ms with steps of 100 and from 1000-5000 ms with steps of 1000 ms.) and processed (thresholding and measuring the overlaid image) using the parameter nucleic acid content (each microbial cell is calculated with equation 1). Each exposure time was compared (chi-square test with alpha 0.05) to other exposure times within the same culture.

To evaluate the optimal exposure time, each exposure time of each different bacterial culture gets a number according to the similarity. The higher the number, the more cultures were sampled in this exposure time (e.g. 10 ms compared to 10 ms gives a 6 because each sample have a similar dataset of 10 ms against 10 ms). Five or more cultures within a set of exposure time indicate that these exposure times are similar for at least 80% of the data (see FIG. 1). The larger the area with numbers 5 or 6 the more likely the optimal exposure time is reached.

Step (iii) of a method of the invention comprises classifying, based on the at least first and second parameter, a cell into one of the following categories: (A) viable cultivable cells, (B) viable non-cultivable cells and (C) most likely dead cells in a microbial population.

Preferably, once the average grey value, the standard deviation and surface area per microbial cell is measured, the nucleic acid content can be calculated on the basis of equation 1, in combination with values for the extent of stretching of the cell based on the surface area, cut off limits which are determined after repeated experiments. These are subsequently correlated to culturing results to determine in which category the cell should be classified.

Cut Off Limits:
(A) Viable cultivable cells with a nucleic acid content value between $>=0.1$ and $<1.0$ and extent of stretching of the cell value between $>=1.0$ and $10$ $\mu m^2$.
(B) Viable non-cultivable cells with a nucleic acid content value of $>-0.2$ and extent of stretching of the cell value of $>=0.5$ $\mu m^2$ minus Viable cultivable cells (A).
(C) Most likely dead cells with a nucleic acid content of $<1.0$ and extent of stretching of the cell value of $<0.5$ $\mu m^2$.
(D) Total number of microbial cells is the sum of (A), (B) and (C).

In a preferred embodiment, step (iii) comprises plotting for each cell said first parameter against said second parameter to obtain distinct populations of cells. See for example FIG. 2. FIG. 3 supports the cut off limits of the viable cultivable microbial cells.

Based on the nucleic acid content classification in step in step (iv) calculating the ratio of the amount of (A) viable cultivable cells, (B) viable non-cultivable cells and (C) most likely dead cells in a microbial sample.

LEGEND TO THE FIGURES

FIG. 1: Six different cultures were stained, imaged (a light titration consisting of the acquisition of digital images at exposure times varied from 10-100 ms with steps of 10 ms, from 100-1000 ms with steps of 100 and from 1000-5000 ms with steps of 1000 ms.) and processed (thresholding and measuring the overlaid image) using the parameter nucleic acid content (each microbial cell is calculated with equation 1). Each exposure time was compared (chi-square test with alpha 0.05) to other exposure times within the same culture. Numbers appear between 1 up till 6. The higher the number, the more cultures were sampled in this exposure time (e.g. 10 ms compared to 10 ms gives a 6 because each sample have a similar dataset of 10 ms against 10 ms). Five or more cultures within a set of exposure time indicate that these exposure times are similar for at least 80% of the data. The optimal exposure time range for this optical system and magnification factor is between 800 and 1000 ms.

FIG. 2: Differences between old and young bacterial cell culture. Graph A displays a young culture and graph B an old culture both were processed by the protocols detecting damaged bacterial cells (squares) and detecting total bacterial cells (diamonds). The horizontal line in the graphs offers the threshold for the extent of stretching of the cell. The vertical line in the graphs offers the threshold for the nucleic acid content value. Images (FIG. 2A' and FIG. 2B') are examples of the intensities captured by the camera (magnification factor of 200 times and an exposure time of 510 ms). A' is a young culture and B' is an old culture.

EXPERIMENTAL SECTION

Materials and Methods

Cultures

For all experiments *Escherichia coli* (DSMZ 301) was used. For assessing the differences between old and fresh bacterial cell cultures, cultivation of bacteria was initiated from a Cryo-bank stored culture in 5 mL TSB (Oxoid, CM0129) for 30 min at room temperature (20° C.). Subsequently 50 µL were subcultured in 5 mL TSB and incubated for 7-9 hours at 37° C. For the fresh bacterial cell culture measurements cultures were used immediately. For creating an old bacterial cell culture, the culture was stored at 5° C. for at least 1 year.

In order to compare the cultivable fraction using the standard culturing techniques and the proposed method, cultivation of bacteria was performed from the Cryo-bank culture in 5 mL TSB (Oxoid, CM0129) for 20 hours at 37° C. 100 µL of this culture were subcultured in 5 mL TSB for 20 hours at 37° C.

Standard Culturing Techniques

Comparing the Cultivable Fractions of *E. coli*

To acquire a cultivable fraction the samples were incubated on Plate Count Agar (PCA) (Oxoid, CM0325). A 10 fold dilution series was prepared and 1 ml of each dilution (in duplicate) was poured into a petri dish and 20 mL of PCA (cooled down to 42-45° C.) were added and stirred well. The plates were incubated for 2 days at 37° C. After incubation the plates were counted manually. Only plates containing more than 30 and less than 300 bacteria were counted.

Detecting Damaged Bacterial Cells

To detect bacteria with damaged cell walls, 10% bacterial cell culture, 70% sodium chloride solution (0.9% (w/v) NaCl) (v/v) and 20% staining solution (0.03 mg/mL propidium iodide (Fluka, Sigma-Aldrich ecno. 2470810) dissolved in Milli-Q water) were mixed well and incubated for 10 min at room temperature in the dark. Subsequently, the mix was centrifuged in a table top centrifuge for 5 min at 6000 rpm. After centrifugation the suspension was replaced by sodium chloride solution (0.9% (w/v) NaCl) (v/v) and gently mixed. 10 µL of the stained bacterial solution were spotted on glass (diagnostic slides, 8 wells/6 mm) and dried on air for 30 min. Each spot was covered with 5 µL mounting medium (Invitrogen, 17224 component H) to prevent the breakdown of the fluorochrome during the storage period (one week to several weeks, in the dark at room temperature).

Detecting Total Numbers of Bacterial Cells:

For the total cell count 10% bacterial cell culture, 10% formaldehyde (37% v/v) and 80% sodium chloride solution (0.9% (w/v) NaCl) (v/v) were mixed well and incubated for 30 min at room temperature. Subsequently, the mix was centrifuged in a table top centrifuge for 5 min at 6000 rpm. After centrifugation the supernatant was replaced using sodium chloride solution and the vial was mixed well. 10 µL of the bacterial solution were spotted on diagnostic slides and air-dried for 30 min. Dehydration (96% (v/v) ethanol) was performed to ensure total water removal and to allow easy transport of the staining dye into the bacteria cells. The propidium iodide staining solution (0.03 mg/mL) was added and samples were incubated for 10 min in the dark at room temperature. The slides were washed using Milli-Q water for 5 min in the dark at room temperature. Slides were air-dried in the dark and each spot was covered with 50 µL mounting medium to prevent the breakdown of the fluorochrome during the storage period (one week to several weeks, in the dark at room temperature).

Figure 1:
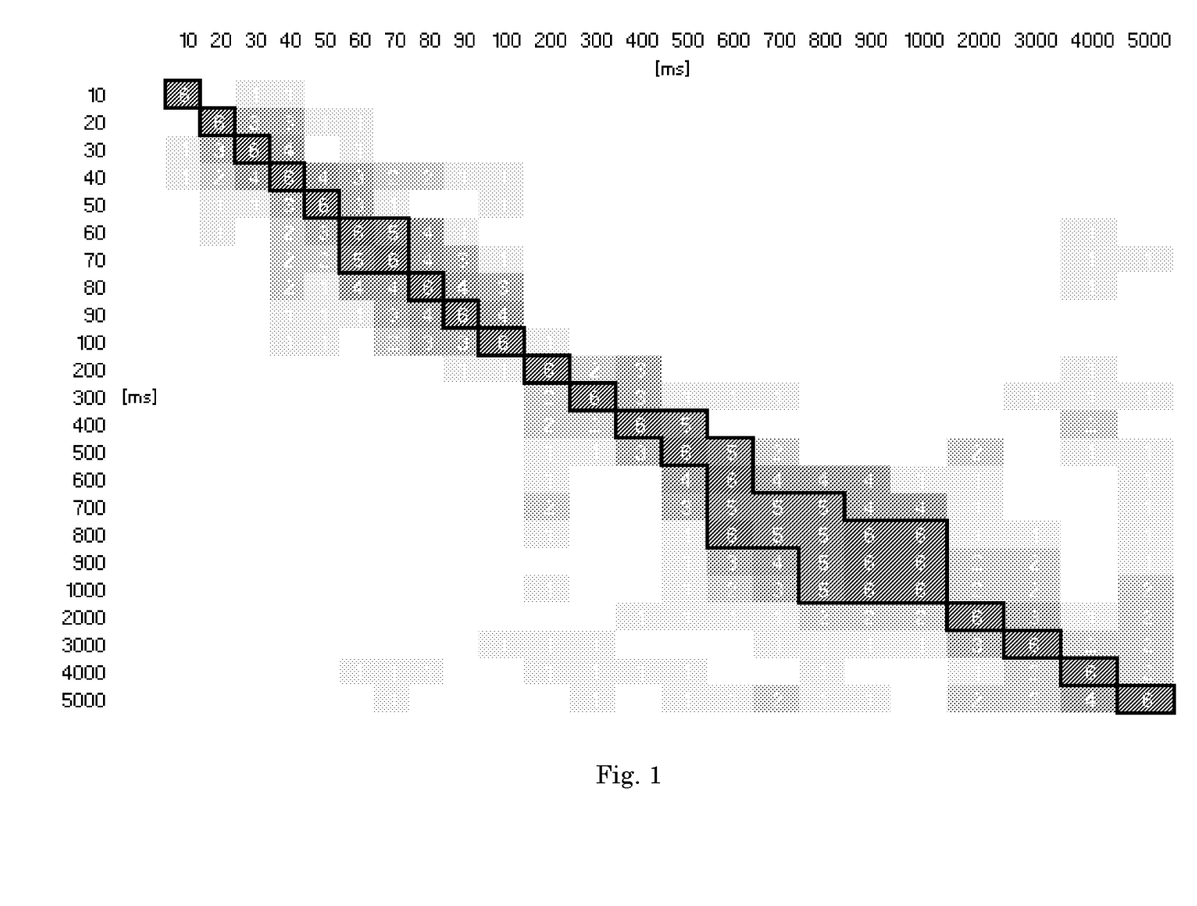

FIG. 1 Experimental Design:

Data Processing:

We used an integration of biological significant variable approach to obtain a binarized image (Tamminga et at, 2016). This approach uses the shift of threshold and counting of noise and objects of interest (OOI) to determine a cut-off value when the count of OOI was larger than the count of the noise. At this point the threshold was determined. The software used was ImageJ version 1.47 m (Abràmoff et al., 2004). Before obtaining a binary image, the minimum value was set to 0 (e.g. if the minimum value in the image was 20, then 20 was subtracted from all grey values of the image). After that a subtract background method was applied (Sternberg, 1983) (this method can handle zero values). Objects that were too small to represent a bacterium (calculated smallest rod (Palumbo et al., 1984) in pixels minus 1 pixel, calculations were based on calibrations per optical system using a micro scale measuring staff) or had a lower intensity than the mean background of the image were not counted. After obtaining a binarized image a feed-back was made to the original image to measure different parameters such as average grey value, standard deviation and the surface of the bacterial cell as well as the average background of the corresponding image.

Clarifying the Parameters:

The three parameters 'average grey value', 'standard deviation' and 'surface of the bacterial cell' were used for the determination of cultivability of each single cell. Nucleic acid content is defined as the modified coefficient of variation (CV), which is the ratio between logarithm of the standard deviation and the logarithm of the average grey value of the bacterial cell (equation 1). The parameters 'average grey value' and 'standard deviation' are independent according to the principal component analysis (coefficient of determination of PCA1 and PCA2 is 0.75). The area of a bacterial cell gives information about the extent of stretching of the cell. The parameters 'extent of stretching of the cell' and 'nucleic acid content' are as well independent according to principal component analysis (coefficient of determination of PCA1 and PCA2 is 0.98). Therefore these parameters can be plotted against each other.

Evaluating Exposure Times:

To evaluate the effect of the exposure time on the parameter nucleic acid content, 6 different bacterial cultures were used and 1 sample of each individual culture was harvested. The samples were processed according detecting total numbers of bacterial cells. After staining, each sample was photographed on 4 different locations on the microscopic slides at different exposure times and a magnification factor of 200×. The images were taken with an Olympus (BH2) microscope with an Olympus mercury lamp (BH2-RFL-T3) and a Lumineria LM135 camera. Then exposure time were varied from 10-100 ms with steps of 10 ms, from 100-1000 ms with steps of 100 and from 1000-5000 ms with steps of 1000.

Data Interpretation:

One parameter was tested: nucleic acid content, this is the ratio between the logarithm of the standard deviation and the logarithm of the mean grey value of the bacterial cell (equation 1).

In this experiment the parameter nucleic acid content was segmented as follow: −0.4-1.1 with steps of 0.15. After segmentation the values per segmentation were expressed as percentages. To evaluate the data a chi-square test with alpha 0.05 was applied as the data were not normal distributed according to the Kolmogorov-Smirnov test ($\alpha=0.05$).

Calculating the Effect of Exposure Time

Each individual sample yields 23 different datasets. These 23 datasets had an increased exposure time (see above) between 10 ms and 5000 ms. To evaluate one dataset against the other 22 datasets of the identical sample for finding similarities, a chi-square test with alpha 0.05 was applied as the data was not normal distributed (according to the Kolmogorov-Smirnov test ($\alpha=0.05$)).

FIG. 2 Experimental Design:

Data processing and clarifying the parameters are described above.

Differences Between Old and Fresh Bacterial Cell Cultures

Both *E. coli* cultures (old (stored at 5° C. for at least 1 year) and fresh (7-9 hours incubation)) were processed using the staining protocol for detecting damaged bacterial cells and total bacterial cells. The extent of stretching of the cell of each individual bacterial cell was plotted against the nucleic acid content of said bacterial cell. The data sets detecting damaged bacterial cells and total bacterial cells were plotted into one graph. This was done to investigate where the damaged bacterial cells are displayed in comparison to the total stained bacteria population. The same graph was made for an old culture.

Figure 2A:
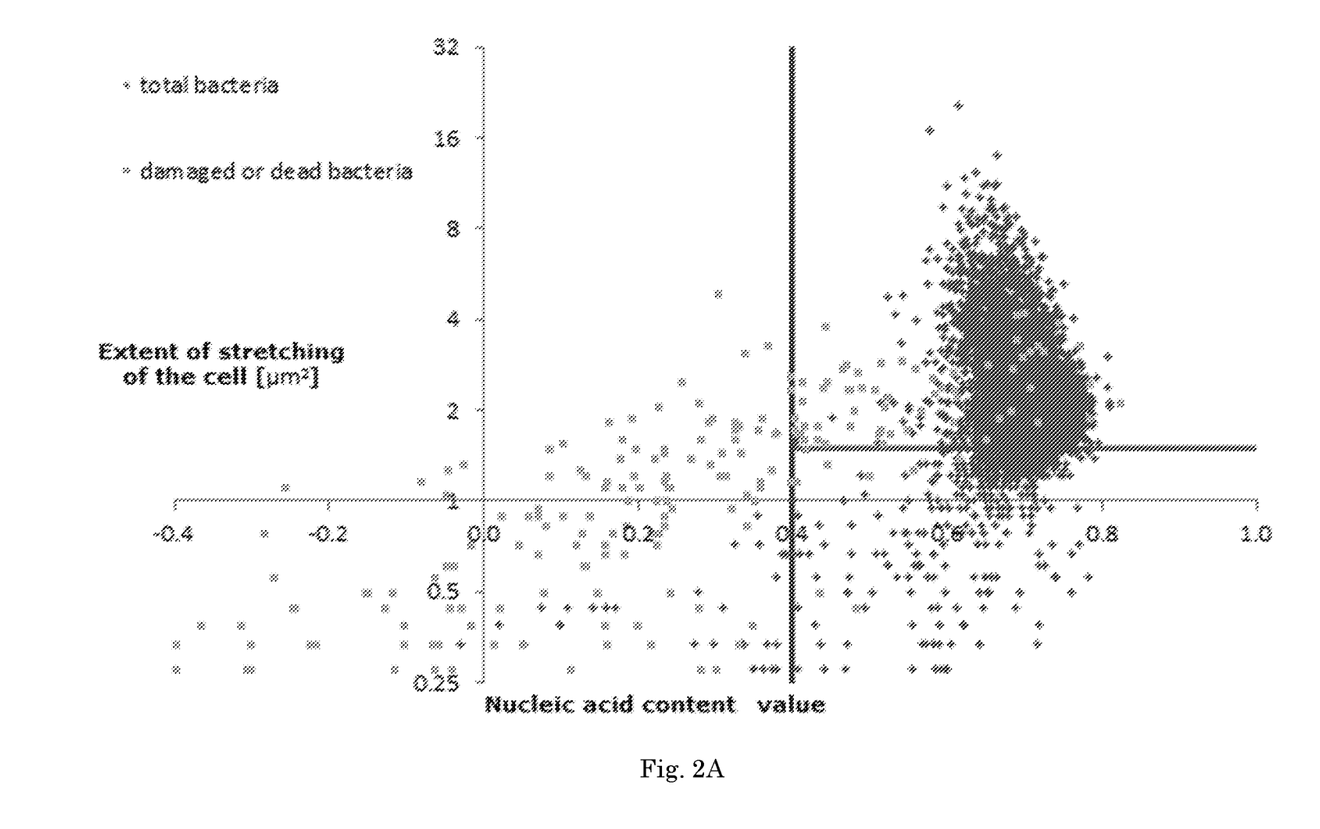
Figure 2B:
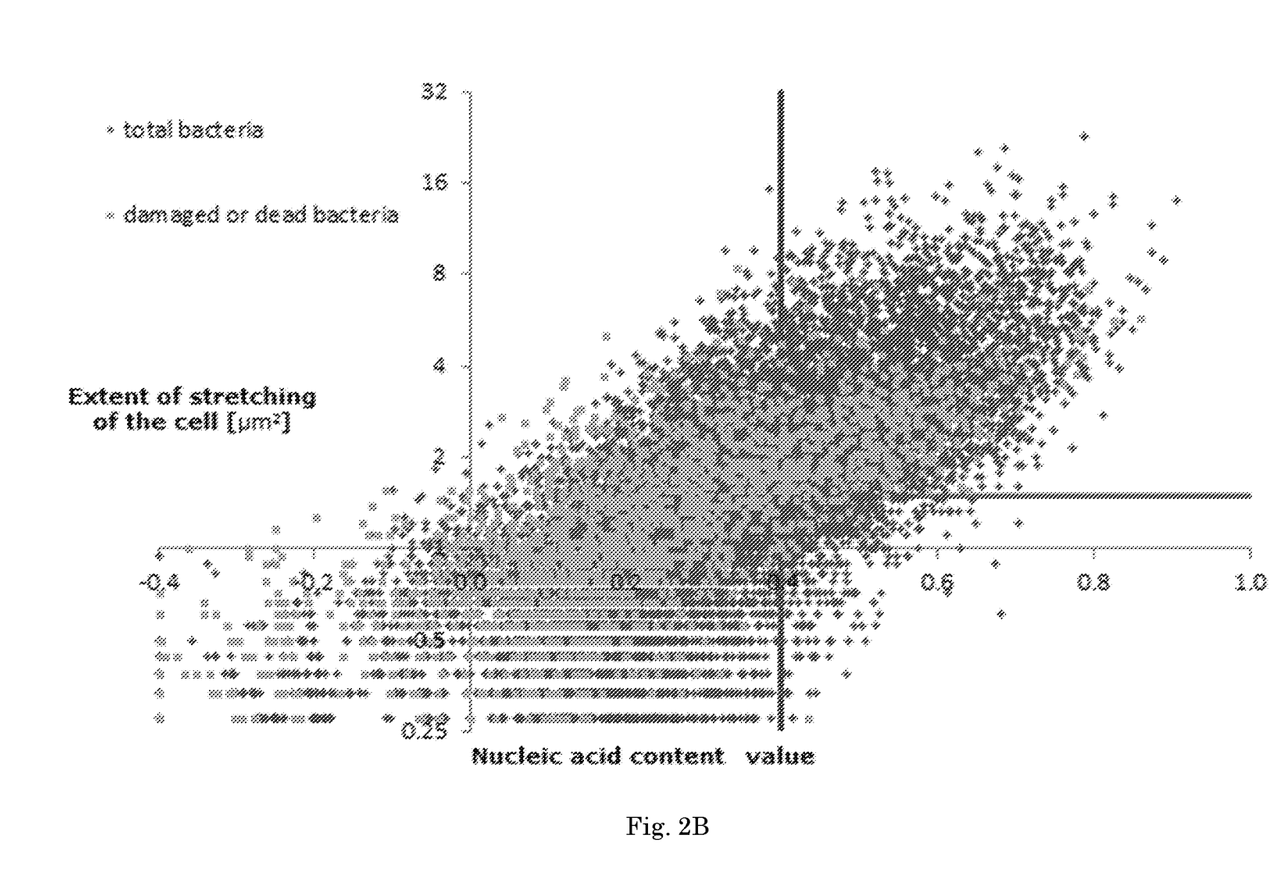
Figure 3:
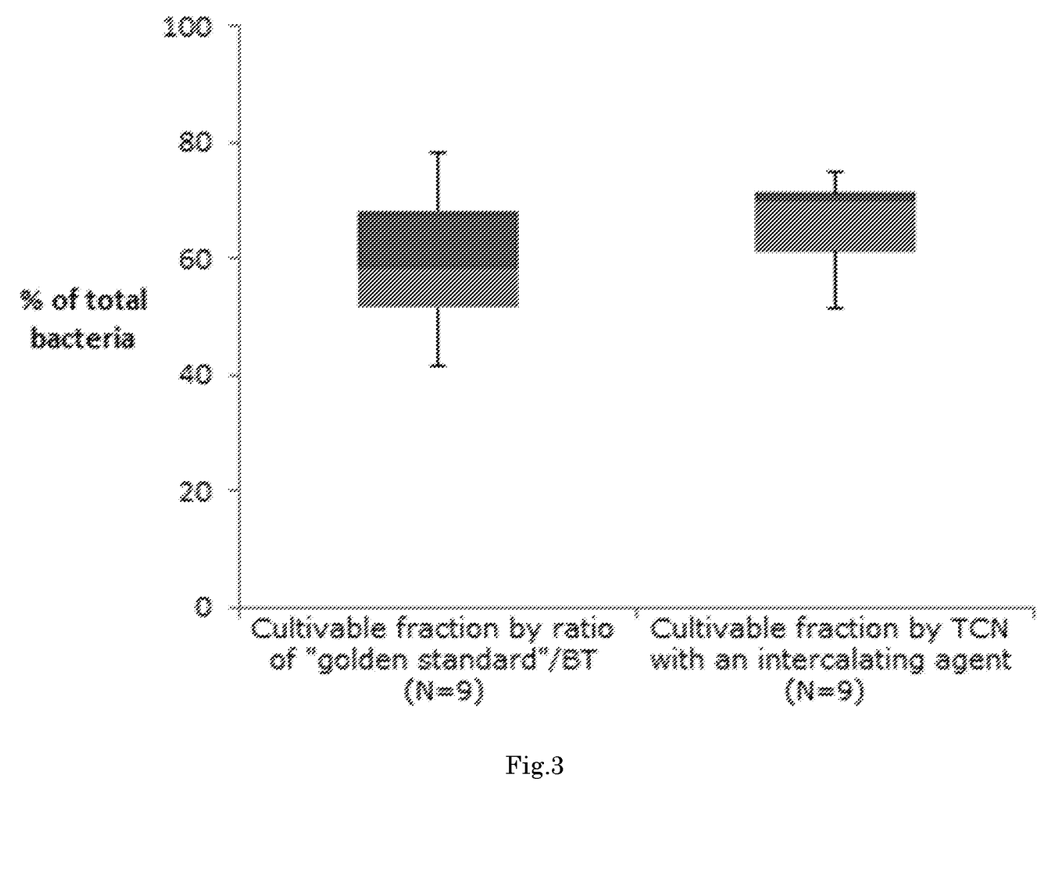
FIG. 3: Comparing the cultivable fraction by ratio of "gold standard"/Bürker Türk counting chamber (BT) and proposed method by total cell number (TCN) with an intercalating agent and the viable cultivable microbial cells (Viable cultivable cells with a nucleic acid content value between $>=0.1$ and $<1.0$ and extent of stretching of the cell value between $>=1.0$ and $10$ $\mu m^2$. Y-axis displays the total bacteria population in percentages.

Data Interpretation:

FIG. 2 presents a distinction between young (FIGS. 2A and A') and old (FIGS. 2B and B') bacterial cell cultures. Additionally FIG. 2 illustrates the distinction between two different staining protocols, namely damaged bacterial cells (squares) and total numbers of bacterial cells (diamonds). Those two staining protocols were tested on the same old and young bacterial cell cultures.

The protocol used for staining the total numbers of bacterial cells (squares) is designed in such a way that all bacteria are permeabilized (treatment with formaldehyde 3.7% and alcohol 96%). Therefore no discrimination between damaged or dead cells and viable cells can be made. The protocol which is used to detect damaged/dead cells is only staining the damaged/dead cells (diamonds)(no treatment with any chemical).

In FIG. 2A a difference between total numbers of bacterial cells and damaged/dead bacterial cells is notable. With these two results we can identify where the damaged/dead bacterial cells and the viable bacterial cells are presented within a young bacterial culture.

In FIG. 2B (old bacterial culture) a smaller difference between total numbers of bacterial cells and damaged/dead bacterial cells is notable. Within an old bacterial cell culture there are more damaged/dead bacterial cells and therefore a larger fraction is stained according to the damaged bacterial cells staining protocol. For the staining protocol total number of bacterial cells the same fraction is stained and positioned within FIG. 2B. Most likely these bacterial cells compared to the results of FIG. 2A are damaged/dead bacterial cells.

The differences between old and young bacterial cell culture is not only visible in the diagrams (FIGS. 2A and 2B), but also in the images of the protocol for staining the total numbers of bacterial cells. (FIG. 2A' young culture, FIG. 2B' old culture). The fluorescence brightness of the bacterial cells is darker within the old bacterial cell culture compared to the bacterial cells of the young culture.

Additionally a threshold value to distinguish the viable and cultivable fraction from the non-viable (damaged/dead) fraction can be applied. The fresh culture (FIG. 2A) which is stained with the protocol detecting total bacterial cells (FIG. 2A, diamonds) has a large group of bacteria projected between a nucleic acid content of 0.1 and 1.0 with an extent of stretching of the cell between 1.0 and 10 $\mu m^2$. In comparison, the protocol detecting damaged bacterial cells (FIG. 2A, squares) shows a group of bacteria projected with a low nucleic acid content of <0.1 with an extent of stretching of the cell value of <1.0 µm².

Confirmation of this low nucleic acid content group is visible in FIG. 2B—the old culture. By focusing only on the stained total bacterial cells (FIG. 2B, diamonds) a large group of bacterial cells with a low nucleic acid content (<0.1) is visible. The protocol detecting damaged bacterial cells (FIG. 2B, squares) shows a considerable overlap with the low nucleic acid content (<0.1) group.

Following these results we suggest that there a threshold value to distinguish the viable and cultivable fraction from the non-viable/dead fraction is applicable. In this specific case the viable cultivable microbial cells has a nucleic acid content between 0.1 and 1.0 with an extent of stretching of the cell between 1.0 and 10 µm².

FIG. 3 Experimental Design:

Data processing and clarifying the parameters are described above.

Comparing the Cultivable Fraction Using the Standard Culturing Technique and the Proposed Method Nine samples were collected from one *E. coli* culture. These were processed using a Bürker Türk counting chamber and the plate count agar method. The cultivable fraction was calculated as follows: cell counts generated by plate count agar method divided by Bürker Türk counting chamber counts. The same nine samples were counted using the staining protocol for total bacterial cells and the data was processed as described above. The cut off was set for viable cultivable microbial cells a nucleic acid content between 0.1 and 1.0 with an extent of stretching of the cell between 1.0 and 10 µm². The cultivable fraction was calculated as follows: cultivable count was divided by the total count.

FIG. 3 presents two boxplots illustrating the percentage of the cultivable fraction. The left boxplot is calculated from the standard culturing technique analyses (Bürker Türk and plate count agar). The right boxplot is calculated from the proposed method. Both data sets (n=9) were normal distributed according to the Kolmogorov-Smirnov test ($\alpha=0.05$). Therefore a two tailed paired two-sample T-test ($\alpha=0.05$) was performed. The cultivable fraction calculated from the standard culturing techniques is statistically equal to the proposed method ($p>0.05$).

REFERENCES

Abràmoff, M. D., Magalhães, P. J., Rain, S A, 2004. Image Processing with ImageJ. Biophotonics Int. 11, 36-41. doi:10.1117/1.3589100

Berney, M., Hammes, F., Bosshard, F., Weilenmann, H. U., Egli, T., 2007. Assessment and interpretation of bacterial viability by using the LIVE/DEAD BacLight kit in combination with flow cytometry. Appl. Environ. Microbiol. 73, 3283-3290. doi:10.1128/AEM.02750-06

Boulos, L., Barbeau, B., Desjardins, R., 1999. Methods LIVE/DEAD® Bac Light E□: application of a new rapid staining method for direct enumeration of viable and total bacteria in drinking water 37, 77-86.

Breeuwer, P., Abee, T., 2000. Assessment of viability of microorganisms employing fluorescence techniques. Int. J. Food Microbiol. 55, 193-200. doi:10.1016/S0168-1605 (00)00163-X Flemming, H., 2013. How dead are "dead" microbes□? A critical discussion.

Hammes, F., Berney, M., Egli, T., 2011. Cultivation-independent assessment of bacterial viability, in: Advances in Biochemical Engineering/Biotechnology. Springer Berlin Heidelberg, pp. 123-150. doi:10.1007/10_2010_95

Oliver, J. D., 2005. The viable but nonculturable state in bacteria. J. Microbiol. 43 Spec No, 93-100. doi:2134 [pii]

Palumbo, A. V, Rublee, P. A., Miklas, J., 1984. Size of Suspended Bacterial Cells and Association of Heterotrophic Activity with Size Fractions of Particles in Estuarine and Coastal. Appl. Environ. Microbiol. 48, 157-164.

Sternberg, S. R., 1983. Biomedical Image Processing. Computer (Long. Beach. Calif.). 16, 22-34. doi:10.1109/MC.1983.1654163

Tamminga, G. G., Paulitsch-Fuchs, A. H., Jansen, G. J., Euverink, G. J. W., 2016. Different Binarization Processes Validated against Manual Counts of Fluorescent Bacterial Cells. J. Microbiol. Methods 128, 118-124. doi:10.1016/j.mimet.2016.07.003

Williams, S. C., Hong, Y., Danavall, D. C. A., Howard-Jones, M. H., Gibson, D., Frischer, M. E., Verity, P. G., 1998. Distinguishing between living and nonliving bacteria: Evaluation of the vital stain propidium iodide and its combined use with molecular probes in aquatic samples. J. Microbiol. Methods 32, 225-236. doi:10.1016/S0167-7012(98)00014-1

Zengler, K., 2009. Central role of the cell in microbial ecology. Microbiol. Mol. Biol. Rev. 73, 712-29. doi: 10.1128/MMBR.00027-09

The invention claimed is:

1. A method for quantifying the cultivability of microbial cells using culture independent parameters, comprising the steps of:
    (i) contacting a sample of microbial cells with a nucleic acid binding fluorescent dye to stain cellular nucleic acids in said microbial cells;
    (ii) subjecting said microbial cells to a fluorescence microscopy imaging method;
    (iii) determining at least a first parameter and a second parameter from the results of the fluorescence microscopy imaging method for each of said microbial cells, said first parameter being the nucleic acid content of said microbial cell and said second parameter being the extent of stretching of each of said microbial cells;
    (iv) classifying, based on said at least first and second parameter, each of said microbial cells as either:
    (A) a viable cultivable cell with a first parameter value with a fluorescence intensity between ≥0.1 and 1.0 and a second parameter value between ≥1.0 and 10 µm²,
    (B) a viable non-cultivable cell with a first parameter value with a fluorescence intensity of ≥—0.2 and a second parameter value of ≥0.5 µm², or
    (C) a most likely dead cell with a first parameter value with a fluorescence intensity of <1.0 and a second parameter value of <0.5 µm²; and
    (v) calculating a ratio for the sample, wherein the ratio is based on at least two of an amount of (A) viable cultivable cells in the sample, an amount of (B) viable non-cultivable cells in the sample and (C) an amount of most likely dead cells in the sample.

2. The method according to claim 1, wherein the sample is selected from the group consisting of water samples, clinical samples, beverages, dairy products, and liquid growth media.

3. The method according to claim 2, wherein the sample is a clinical sample and the clinical sample is selected from the group consisting of respiratory sample, urogenital sample, reproductive tract sample, central nervous system sample, urine, blood, dermal, plasma, serum, saliva, wound tissue, wound exudate, biopsy, faeces, liquid microbial cultures and solid tissue samples.

4. The method according to claim 1, wherein said microbial cells comprise bacterial cells, yeast cells, fungal cells, parasitic cells or any combination thereof.

5. The method according to claim 1, wherein step (i) comprises fixation and dehydration of said microbial cells.

6. The method according to claim 1, wherein step (i) comprises staining said microbial cells with an intercalating agent.

7. The method according to claim 1, wherein step (ii) comprises subjecting said microbial cells to a filter cytometry process to stain, scan, detect, and count said microbial cells on the surface area of a membrane filter.

8. The method according to claim 7, wherein said filter cytometry process comprises the steps of:
 a) applying a predetermined volume of the sample on a filter;
 b) imaging said microbial cells on the surface area of the membrane filter and creating a filter image; and
 c) analysing the filter image for quantification of said microbial cells on the filter, wherein the step of analysing comprises determining the optimal threshold for separating said microbial cells from the background in the filter image.

9. The method according to claim 8, wherein determining the optimal threshold in step c) comprises:
 i. thresholding the filter image using a range of thresholds;
 ii. determining the ratios of selected and unselected objects for the range of thresholded images, wherein an object with a size larger than a predetermined lower threshold is selected; and
 iii. designating a threshold from the range of thresholds resulting in the highest ratio as the optimal threshold.

10. The method according to claim 8, wherein at least steps (a) and (b) are executed at separate locations in a device for automatic filter cytometry, wherein the filter is automatically moved between said locations and wherein said steps can be executed simultaneously on at least two separate filters.

11. The method according to claim 1, wherein determining said at least first and second parameter comprises analysis of a crude fluorescence microscopic image using a thresholding algorithm to obtain a binary filter image, and making an overlay of the binary and crude filter image to determine the average grey value, standard deviation and surface area of said microbial cells.

12. The method according to claim 1, wherein step (iv) comprises plotting for each microbial cell said first parameter against said second parameter to obtain distinct populations of said microbial cells.

13. The method according to claim 6, wherein the intercalating agent comprises at least one of propidium iodide (PI), acridine orange, SYBR Green I, YO-PRO-1, TOTO-3, and TO-PRO-3.

* * * * *